(12) United States Patent
Rasochova et al.

(10) Patent No.: US 11,154,522 B2
(45) Date of Patent: Oct. 26, 2021

(54) COMPOSITIONS AND METHODS FOR TREATING ACNE VULGARIS

(71) Applicant: Dermala Inc., San Diego, CA (US)

(72) Inventors: Lada Rasochova, Del Mar, CA (US); Edward T Kisak, San Diego, CA (US); John Newsam, La Jolla, CA (US)

(73) Assignee: Dermala Inc., San Diego, CA (US)

( * ) Notice: Subject to any disclaimer, the term of this patent is extended or adjusted under 35 U.S.C. 154(b) by 0 days.

(21) Appl. No.: 16/302,640

(22) PCT Filed: May 25, 2017

(86) PCT No.: PCT/US2017/034533
§ 371 (c)(1),
(2) Date: Nov. 17, 2018

(87) PCT Pub. No.: WO2017/205659
PCT Pub. Date: Nov. 30, 2017

(65) Prior Publication Data
US 2020/0129462 A1 Apr. 30, 2020

Related U.S. Application Data

(60) Provisional application No. 62/342,060, filed on May 26, 2016.

(51) Int. Cl.
| A61K 31/194 | (2006.01) |
| A61P 17/10 | (2006.01) |
| A61K 9/00 | (2006.01) |
| A61K 9/107 | (2006.01) |

(52) U.S. Cl.
CPC ............ *A61K 31/194* (2013.01); *A61P 17/10* (2018.01); *A61K 9/0014* (2013.01); *A61K 9/107* (2013.01)

(58) Field of Classification Search
CPC .... A61K 31/194; A61K 9/0014; A61K 9/107; A61K 31/60; A61K 45/06; A61K 8/4973; A61K 8/37; A61K 8/39; A61K 8/49; A61K 8/362; A61K 47/10; A61P 17/10; A61Q 19/008
See application file for complete search history.

(56) References Cited

U.S. PATENT DOCUMENTS

| 6,346,537 B1 | 12/2002 | Hata et al. |
| 9,101,662 B2 | 8/2015 | Tamarkin et al. |
| 2014/0079657 A1 | 3/2014 | Resnick et al. |

*Primary Examiner* — Sahar Javanmard
(74) *Attorney, Agent, or Firm* — Torrey Pines Law Group, PC

(57) ABSTRACT

Disclosed are compositions, methods of treatment using the compositions and methods of preparing the compositions for the treatment of acne vulgaris. The compositions include succinic acid, Brij®-30 and a molecular penetration enhancer in a pharmaceutically acceptable preparation. The molecular penetration enhancer may include one or more of DMSO, dimethyl isosorbide, lauryl lactate and isopropyl myristate.

8 Claims, 6 Drawing Sheets

FIG. 3

| Percent Dose Delivery | DerF1 | DerF2 | DerF3 | DerF4 | DerF5 | DerF6 |
|---|---|---|---|---|---|---|
| Transdermal | | | | | | |
| 4hrs | 0.22 | 0.41 | 0.26 | 0.15 | 2.63 | 0.56 |
| 8hr | 0.21 | 1.55 | 0.29 | 0.15 | 11.30 | 2.53 |
| 20hrs | 1.60 | 22.27 | 9.26 | 3.76 | 42.24 | 24.26 |
| Epidermis | 1.05 | 15.36 | 15.05 | 6.01 | 13.92 | 15.94 |
| Dermis | 0.39 | 22.59 | 15.08 | 4.99 | 12.02 | 14.85 |
| StdErr | | | | | | |
| Transdermal | | | | | | |
| 4hrs | 0.03 | 0.05 | 0.04 | 0.01 | 1.24 | 0.06 |
| 8hr | 0.02 | 0.28 | 0.03 | 0.01 | 3.23 | 0.35 |
| 20hrs | 0.52 | 2.73 | 4.44 | 0.47 | 5.72 | 4.16 |
| Epidermis | 0.19 | 3.39 | 1.40 | 1.38 | 1.54 | 2.22 |
| Dermis | 0.10 | 3.87 | 1.43 | 1.50 | 2.33 | 0.69 |

FIG. 6

| Delivered dose in (µg/cm2) | DerF1 | DerF2 | DerF3 | DerF4 | DerF5 | DerF6 |
|---|---|---|---|---|---|---|
| Transdermal | | | | | | |
| 4hrs | 0.97 | 1.59 | 0.96 | 0.62 | 11.08 | 2.28 |
| 8hr | 0.91 | 5.99 | 1.08 | 0.62 | 47.57 | 10.36 |
| 20hrs | 6.91 | 85.78 | 34.92 | 15.11 | 177.80 | 99.35 |
| Epidermis | 4.55 | 59.15 | 56.76 | 24.19 | 58.60 | 65.28 |
| Dermis | 1.70 | 87.02 | 56.90 | 20.09 | 50.61 | 60.79 |
| StdErr | | | | | | |
| Transdermal | | | | | | |
| 4hrs | 0.13 | 0.20 | 0.15 | 0.04 | 5.23 | 0.24 |
| 8hr | 0.08 | 1.07 | 0.11 | 0.04 | 13.59 | 1.45 |
| 20hrs | 2.25 | 10.52 | 16.77 | 1.90 | 24.09 | 17.06 |
| Epidermis | 0.84 | 13.04 | 5.29 | 5.53 | 6.48 | 9.09 |
| Dermis | 0.44 | 14.91 | 5.40 | 6.01 | 9.80 | 2.83 |

COMPOSITIONS AND METHODS FOR TREATING ACNE VULGARIS

CROSS-REFERENCE TO RELATED APPLICATIONS

This application claims priority from U.S. Provisional Application Ser. No. 62/342,060 filed on May 26, 2016, which is incorporated herein by reference in its entirety.

STATEMENT REGARDING FEDERALLY SPONSORED RESEARCH OR DEVELOPMENT

Not Applicable.

FIELD OF INVENTION

The present invention is related to compositions and methods for treating acne vulgaris and, in particular, to topical compositions and methods based upon compositions of succinic acid, a polyalkylene glycol alkyl ether such as Brij®-30 and a molecular penetration enhancer.

INTRODUCTION

Acne is a significant inflammatory skin disorder and it is considered the most common skin disorder. Acne affects about 50 million people in the US. It is highly common among adolescents, affecting up to 95% of men and 83% of women in that age group. In approximately 10% of cases, acne has been reported to become severe nodulocystic acne with the potential of producing lifelong disfiguring scars. Acne lesions typically recur for years. Therefore, acne is considered a chronic disease.

The psychosocial morbidity associated with acne is important and includes depression and suicidal thoughts. In addition to impact on patient's quality of life, the economic burden of acne treatment is significant.

Currently available treatments for acne are insufficient. Treatment options for acne vulgaris suffer from significant side effects and none provide complete remediation. Potential side effects include skin irritation evidenced by burning, erythema, peeling, dryness, and contact allergy. Antibiotics have attendant side effects that range from colitis, vaginal candidiasis, and photosensitivity to the development of bacterial resistance and cross-resistance. Thus, there is a need to develop new therapies that are more effective and/or produce reduced side effects.

SUMMARY OF INVENTION

Accordingly, the applicants herein have succeeded in devising new compositions and methods for treating acne vulgaris. The compositions comprise succinic acid, a polyalkylene glycol alkyl ether such as Brij®-30 and a molecular penetration enhancer, in a pharmaceutically acceptable preparation. The molecular penetration enhancer may comprise one or more of dimethyl sulfoxide ("DMSO"), dimethyl isosorbide, lauryl lactate and isopropyl myristate. Surprisingly, the new compositions substantially improve the delivery of succinic acid to the epidermis and dermis. Further, the new compositions may deliver an approximately five-fold greater fraction of the dose of succinic acid to the epidermis and dermis than that of succinic acid in a typical topical vehicle in absence of Brij®-30 and a molecular penetration enhancer. At the same time, systemic delivery and exposure are limited.

Thus, in various embodiments, the present invention includes a topical composition for treating acne vulgaris in which the composition comprises succinic acid, Brij®-30 and a molecular penetration enhancer, in a pharmaceutically acceptable preparation. The molecular penetration enhancer may be one or more of DMSO, dimethyl isosorbide, lauryl lactate and isopropyl myristate. In various embodiments, the compositions of the present invention deliver succinic acid to the epidermis and/or dermis in an amount of about two-fold and, in particular, about five-fold greater than that of succinic acid in vehicle in absence of Brij®-30 and a molecular penetration enhancer.

In various embodiments, the present invention also includes a method of treating acne vulgaris. The method includes administering to a subject in need thereof, a topical composition including succinic acid, Brij®-30 and a molecular penetration enhancer, in a pharmaceutically acceptable preparation. The molecular penetration enhancer may comprise one or more of DMSO, dimethyl isosorbide, lauryl lactate and isopropyl myristate.

In various additional embodiments, the present invention includes a method of preparing a topical formulation for treatment of acne vulgaris. The method includes combining succinic acid, Brij®-30 and a molecular penetration enhancer, in a pharmaceutically acceptable preparation. The molecular penetration enhancer may comprise one or more of DMSO, dimethyl isosorbide, lauryl lactate and isopropyl myristate.

In various embodiments, the succinic acid may be present in the compositions and in methods based upon the compositions, in an amount of from about 0.1 w/w % up to about 20 w/w % and, in particular, in an amount of about 5 w/w %. In another embodiment, succinic acid is present in an amount of about 0.5-4 w/w %.

In various embodiments, the Brij®-30 may be present in the compositions and methods based upon the compositions, in an amount of from about 0.1 w/w % up to about 20 w/w % and, in particular, in an amount of about 5 w/w %.

In various embodiments, the molecular penetration enhancer may be present in the compositions and methods based upon the compositions, in an amount of from about 0.1 w/w % up to about 50 w/w % and, in particular, in an amount of from about 4 w/w % up to about 30 w/w %.

These and other features, aspects and advantages of the present teachings will become better understood with reference to the following description, examples and appended claims.

BRIEF DESCRIPTION OF THE DRAWINGS

Those of skill in the art will understand that the drawings, described below, are for illustrative purposes only. The drawings are not intended to limit the scope of the present teachings in any way.

FIG. 3 is a tabulation illustrating the percentage of the applied dose of succinic acid that is delivered to the epidermis, the dermis and transdermally at 4, 8, and 20 hrs post application with standard error (StdErr) indicated.

FIG. 6 is a tabulation illustrating the amount of succinic acid that is delivered to the epidermis, the dermis and transdermally in μg/cm² at 4, 8, and 20 hrs post application with standard error (StdErr) indicated.

DETAILED DESCRIPTION

Figure 1:
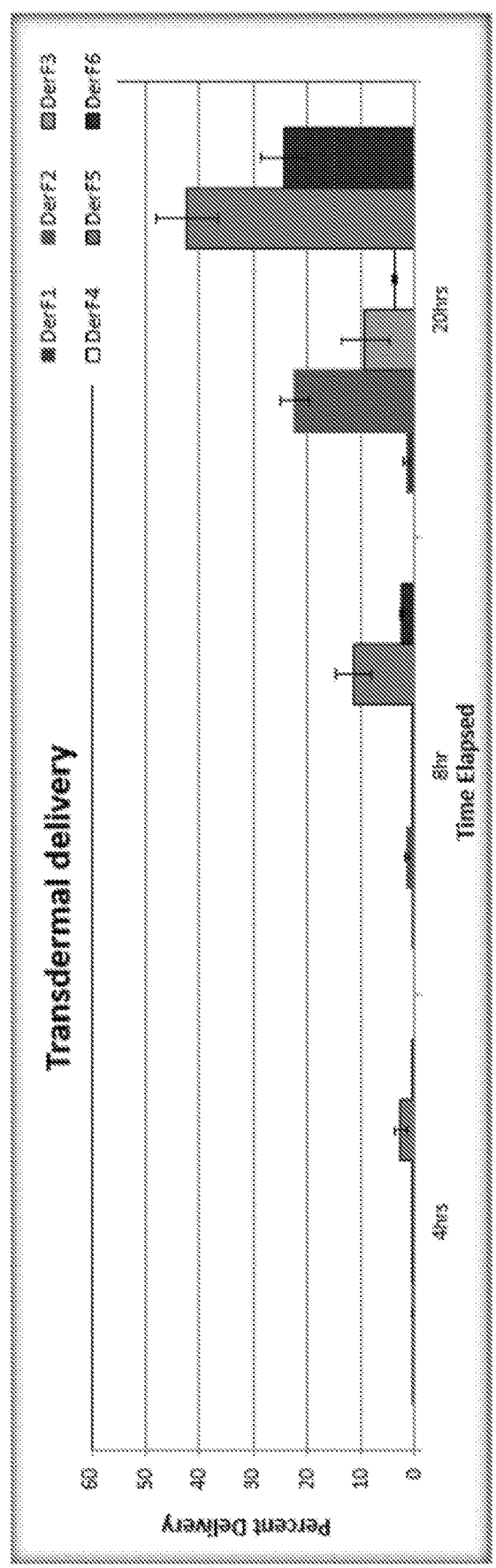
FIG. 1 is a bar chart illustrating the percentage of the applied dose of succinic acid that is delivered transdermally at 4, 8, and 20 hrs post application (standard error is shown; DerF5 is largest bar in each time point).

As used herein, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

As used herein, the term "about" is intended to refer to a range of values above and below a stated value such as for example, values encompassing 10% below up to 10% above a stated value.

The term "and/or" is intended to mean either or both of two recited elements.

"Active pharmaceutical ingredient" ("API") refers to a substance, in particular an agent for the treatment of acne, in a pharmaceutical composition that is delivered for a desired effect. API may include succinic acid, salicylic acid, antibiotic, benzoyl peroxide, azelaic acid, retinoid, or other API used for the treatment of acne. One of skill in the art is able to identify such other APIs.

As used herein, the term "combination" refers to a composition of two or more substances. In the present invention, a combination of substances may include succinic acid, another API for the treatment of acne, Brij®-30 and a molecular penetration enhancer such as one or more of DMSO, dimethyl isosorbide, lauryl lactate and isopropyl myristate. The Brij®-30 and a molecular penetration enhancer may serve as part of a carrier system for delivering succinic acid to the epidermis and/or dermis.

The term "pharmaceutical composition" or 'pharmaceutical preparation" refers to a composition that combines an API with a pharmaceutically acceptable carrier such that the composition is suitable for therapeutic use in vitro, in vivo or ex vivo.

As used herein, the term "pharmaceutically acceptable carrier" encompasses any suitable pharmaceutical carriers, such as a phosphate buffered saline solution, water, and emulsions, such as an oil/water or water/oil emulsion, various types of wetting agents and the like. The compositions also can include stabilizers and preservatives. Examples of carriers, stabilizers and adjuvants, can be found in Remington: The Science and Practice of Pharmacy, Lippincott Williams & Wilkins, Twenty-First edition (May 19, 2005).

A number of carrier systems have been developed, in particular for topical application, including by way of non-limiting examples, vesicular systems such as liposomes, niosomes, ethosomes and transfersomes. (Arora, S. et al., Dermal delivery of drugs using different, vesicular carriers: A comparative review, *J Pharm.* 2012; 6:237-44).

One such vesicular carrier system may include a niosome. As used herein, the term niosome refers to unilamellar or multilamellar vesicles in which an aqueous phase is encapsulated in highly ordered bilayer made up of nonionic surfactant (Vyas, J. et al., "Development of topical niosomal gel of benzoyl peroxide," *International Journal of Nanotechnology*, vol. 2011, Article ID 503158, 6 pages, 2011). They are nonionic surfactant vesicles by which skin penetration and accumulation are increased in the superficial skin strata (Manconi, M. et al., Niosomes as carriers for tretinoin: III. A study into the in vitro cutaneous delivery of vesicle-incorporated tretinoin, *International Journal of Pharmaceutics*, 2006 311(1-2):11-19.). (Vyas, A. et al., Carrier-Based Drug Delivery System for Treatment of Acne, *The Scientific World Journal*, 2014 Feb. 9; 2014:276260. doi: 10.1155/2014/276260. eCollection 2014.) Commonly used non-ionic surfactants include Span® compounds which are sorbitan alkyl esters, Tween® compounds which are polyethoxylated alkyl sorbitan esters and Brij® compounds which are polyoxypropylene glycol alkyl ethers. Brij® compounds may be represented by the following formula:

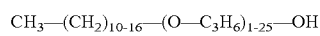

$$CH_3-(CH_2)_{10\text{-}16}-(O-C_3H_6)_{1\text{-}25}-OH$$

One such Brij® compound is Brij®-30 which can be represented by the following formula:

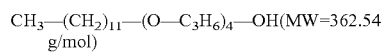

$$CH_3-(CH_2)_{11}-(O-C_3H_6)_4-OH (MW=362.54 \text{ g/mol})$$

The carrier system of the present invention (the "Carrier System") may also include a molecular penetration enhancer. The molecular penetration enhancer is a substance or combination of substances that increase the delivery of an API to the epidermis and/or dermis or transdermally. Molecular penetration enhancers that are disclosed for use in the present invention include, but are not limited to one or more of DMSO, dimethyl isosorbide, lauryl lactate and isopropyl myristate.

Unless otherwise indicated, concentrations are given as percentages of weight by weight, i.e. w/w %. Weight percentages (w/w %) for combination formulations are calculated as follows:

$$\text{mass \% } a = \text{mass}(a) \div (\text{mass}(a) + \text{mass}(b) + \text{mass}(c) + \ldots) \times 100 (\text{w/w \%}).$$

Compositions

The present invention includes compositions, treatment methods and formulation methods based upon compositions that include succinic acid and a carrier system. The carrier system may include a nonionic surface active agent such as, for example, Brij®-30. The carrier system may also include one or more molecular penetration enhancers.

In various of the above embodiments, the succinic acid may be present in the compositions and methods based upon the compositions, in an amount suitable for delivering from about 0.1 mM to about 1M succinic acid to the epidermis and/or dermis, and, in particular, in an amount suitable for delivering from about 5 mM to 1M to the epidermis and/or dermis.

The surprising improvement in delivery of succinic acid to the epidermis and/or dermis by the compositions of the present invention is also illustrated in the Examples section below. The compositions of the present invention, in various embodiments, may deliver succinic acid to the epidermis and/or dermis in an amount greater than that of succinic acid in vehicle in absence of Brij®-30, and a molecular penetration enhancer. This may be an amount of about two-fold greater, about three-fold greater, about four-fold greater or as illustrated in the Examples section below, about five-fold greater than that of succinic acid in vehicle in absence of Brij®-30 and a molecular penetration enhancer.

In various embodiments, the amount of succinic acid in the composition may be from about 0.1 w/w % up to about 20 w/w % and, in particular, from about 0.1, about 0.2, about 0.5, about 0.75 or about 1 w/w % up to about 2, about 3, about 4, about 5, about 7.5, about 10, about 15 or about 20 w/w %. In various embodiments, the amount of succinic acid in the composition may be about 0.1, about 0.2, about 0.5, about 0.75, about 1, about 2, about 3, about 4, about 5, about 6, about 7, about 8, about 9, about 10, about 11, about 12, about 13, about 14, about 15, about 16, about 17, about 18, about 19 or about 20 w/w %.

The compositions of the present invention include succinic acid and a carrier system including the nonionic surfactant, Brij®-30 as well as a molecular penetration enhancer. In various embodiments, Brij®-30 may be present in the compositions in an amount of from about 0.1 w/w % up to about 20 w/w % and, in particular, from about 0.1, about 0.2, about 0.5, about 0.75 or about 1 w/w % up to about 2, about 3, about 4, about 5, about 7.5, about 10, about 15 or about 20 w/w %. In various embodiments, the amount of Brij®-30 in the compositions may be about 0.1, about 0.2, about 0.5, about 0.75, about 1, about 2, about 3, about 4, about 5, about 6, about 7, about 8, about 9, about 10, about 11, about 12, about 13, about 14, about 15, about 16, about 17, about 18, about 19 or about 20 w/w %.

In various embodiments, second molecular penetration enhancer may be present in the compositions and methods based upon the compositions, in an amount of from about 0.1 w/w % up to about 30 w/w % and, in particular, from about 0.1, about 0.2, about 0.5, about 0.75, about 1 or about 2 w/w % up to about 3, about 4, about 5, about 7.5, about 10, about 15, about 20, about 25 or about 30 w/w %. In various embodiments, the amount of molecular penetration enhancer in the compositions may be in an amount of about 0.1, about 0.2, about 0.5, about 0.75, about 1, about 2, about 3, about 4, about 5, about 6, about 7, about 8, about 9, about 10, about 11, about 12, about 13, about 14, about 15, about 16, about 17, about 18, about 19, about 20, about 25 or about 30 w/w %.

In various embodiments, if the penetration enhancer is DMSO, it may be present in the compositions and methods based upon the compositions, in an amount of from about 0.1 w/w % up to about 50 w/w % and, in particular, from about 0.1, about 0.2, about 0.5, about 0.75, about 1, about 2 w/w % up to about 3, about 4, about 5, about 7.5, about 10, about 15, about 20, about 30 or about 50 w/w %. In various embodiments, the amount of DMSO in the compositions may be about 0.1, about 0.2, about 0.5, about 0.75, about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45 or about 50 w/w %.

The compositions of the present invention may be in the form of solutions, creams, gels, lotions, foams or other formats suitable for administration to the skin and that can stabilize the compositions and deliver them to the affected area of epidermis and/or dermis following topical applications.

The pharmaceutically acceptable preparations of the present invention may also contain ingredients that include, but are not limited to, saline, aqueous electrolyte solutions, ethanol, diisopropyl adipate, sodium lauryl sulfoacetate; ionic and nonionic osmotic agents such as sodium chloride, potassium chloride, glycerol, propylene glycol and dextrose; pH adjusters and buffers such as salts of hydroxide, phosphate, citrate, acetate, borate; and trolamine; antioxidants such as salts, acids and/or bases of bisulfate, sulfite, metabisulfite, thiosulfite, ascorbic acid, acetyl cysteine, cystein, glutathione, butylated hydroxyanisole, butylated hydroxytoluene, tocopherols, and ascorbyl palmitate; compounds such as lecithin, phospholipids; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using preservatives, including, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

Methods of Treatment

The methods of treatment of the present invention are useful for the treatment of skin diseases including acne vulgaris. Treatment of acne vulgaris may be by topically administering to a subject a composition that includes the compositions of the present invention.

The compositions of the present invention can be administered at a variety of intervals. In some instances, administration may be once a day. In other instances, administration can be less or more frequently, such as 1, 2, 3, or 4 times a day, 1 time every 2 days, or once a week.

The treatment methods may be monitored by following any of the pathogenic aspects of acne vulgaris including increase of the sebum excretion, keratinization of infrainfundibulum, bacterial colonization of the follicle and/or inflammation. (See Aydemir, E., Acne Vulgaris, *Tsrk Ped Ars* 2014; 49: 13-16).

Formulation Methods

Formulation methods known in the art may be used to prepare the compositions of the present invention. For example, a one-batch formulation method may be used in which the components of the pharmaceutical preparation may be combined in a single container and the components may be added to the container simultaneously or consecutively.

Preparation of emulsions may include some form of energy input such as from trituration, homogenization, agitation or heat. Typical methods that may be used for preparing emulsions include comminution by agitation, comminution by ultrasound, membrane emulsification, homogenization, condensation techniques and the like.

EXAMPLES

Aspects of the present teachings may be further understood in light of the following examples, which should not be construed as limiting the scope of the present teachings in any way.

Example 1

This example illustrates epidermal and dermal distribution and transdermal delivery of succinic acid.

Epidermal and dermal distribution and transdermal delivery of succinic acid from six (6) formulations were determined using Franz diffusion cells ("FDC"s) with human cadaver skin. Molecular penetration enhancers were formulated with a base formulation.

Skin from a single donor was stored frozen at −20° C. until needed. The skin was removed from the freezer, allowed to equilibrate to room temperature, and then cut to ~2 cm×2 cm pieces before testing. FDCs with a 3.3 ml receiver volume and 0.55 cm² diffusional area were used. De-aerated isotonic phosphate buffered saline solution at pH 7.4 (PBS) containing 0.01% NaN₃ was used as a solvent system for the receptor well medium ("Receptor Fluid"). Receptor wells were filled with the Receptor Fluid. The upper flange of the FDC receptor well was coated with vacuum grease to ensure a complete seal. Pieces of skin were mounted on the receptor cells, the conventional donor wells applied, and the assembly clamped together with uniform pressure using a pinch clamp. After assembly of the FDC, the skin was allowed to hydrate for 20 minutes in contact with the receptor fluid. Any FDCs that evidenced any leakage during this period were discarded. The integrity and quality of the skin was tested prior to application of the test formulations through measurement of the transdermal flux of tritiated water. Skin pieces evidencing an excessively high tritiated water flux were discarded and the tritiated water fluxes of accepted skin pieces was used to guide the distribution of formulation samples over the skin piece set. After removal of the tritiated water samples from the donor wells, the clamp and donor wells were removed. The skin was tapped dry with a KimWipe® and the receptor well solutions was replenished with fresh receptor well medium. Six replicates of each of the formulations were examined, in a batch of 36 FDC's; each test formulation was applied at a quasi-infinite dose of 20 μL cm² on skin maintained at 32° C. throughout the experiment. The Receptor Fluid was stirred with a magnetic stir bar throughout. A sample was abstracted from each receptor well at each of 4, 8 and 20 h, the receptor well being replenished with fresh Receptor Fluid. The concentration of succinic acid in each receptor well sample was assayed by a verified LC-MS analytical method. At the end of the experiment (20 h), residual formulation was removed from the skin exterior with a pipette. The FDCs were then be disassembled and the skin washed twice with EtOH-Water 50-50 and wiped dry with a KimWipe®. The successive topmost layers of the stratum corneum were removed by three (3) times applying cellophane tape to the skin and then pulling off the tape. Tape strippings were discarded, the material present in those peripheral layers being considered absorbed only superficially. The epidermal and dermal layers were separated, using mild heating if required. The epidermal and dermal sections were placed into 4 ml glass vials. DMSO was used as an extraction solvent ("Extraction Solvent") for succinic acid from epidermal and dermal tissue. Two ml of the Extraction Solvent was added to each vial and the vials allowed to incubate for 24 h. At the end of the extraction period, aliquots of the Extraction Solvent were drawn, filtered and analyzed by LC-MS.

Formulations tested are shown in Table 1.

TABLE 1

Formulations tested in skin penetration studies using Franz cells.

| | Formulation name | | | | | |
|---|---|---|---|---|---|---|
| | DerF1 | DerF2 | DerF3 | DerF4 | DerF5 | DerF6 |
| Dosing (ul): | 5 | 5 | 5 | 5 | 5 | 5 |
| wt % Succinic Acid | 4.76 | 4.24 | 4.15 | 4.42 | 4.63 | 4.5 |
| Ingredient: | mg | mg | mg | mg | mg | mg |
| Succinic Acid | 5 | 5 | 5 | 5 | 5 | 5 |
| Water | 80 | 75 | 75 | 75 | 30 | 30 |
| Ethanol | 10 | 10 | 10 | 10 | 20 | 30 |
| Propylene Glycol | 10 | 5 | 10 | 10 | 15 | 5 |
| Dimethyl sulfoxide | | 15 | 5 | | 30 | 20 |
| Dimethyl isosorbide | | 5 | 12.5 | | | 10 |
| Isopropyl myristate | | | | | | 5 |
| Lauryl lactate | | | | 4 | | |
| Brij 30 | | 3 | 3 | | 4 | 6 |
| Diisopropyl adipate | | | | 10 | | |
| Sodium lauryl sulfoacetate | | | | 3 | | |

Figure 2:
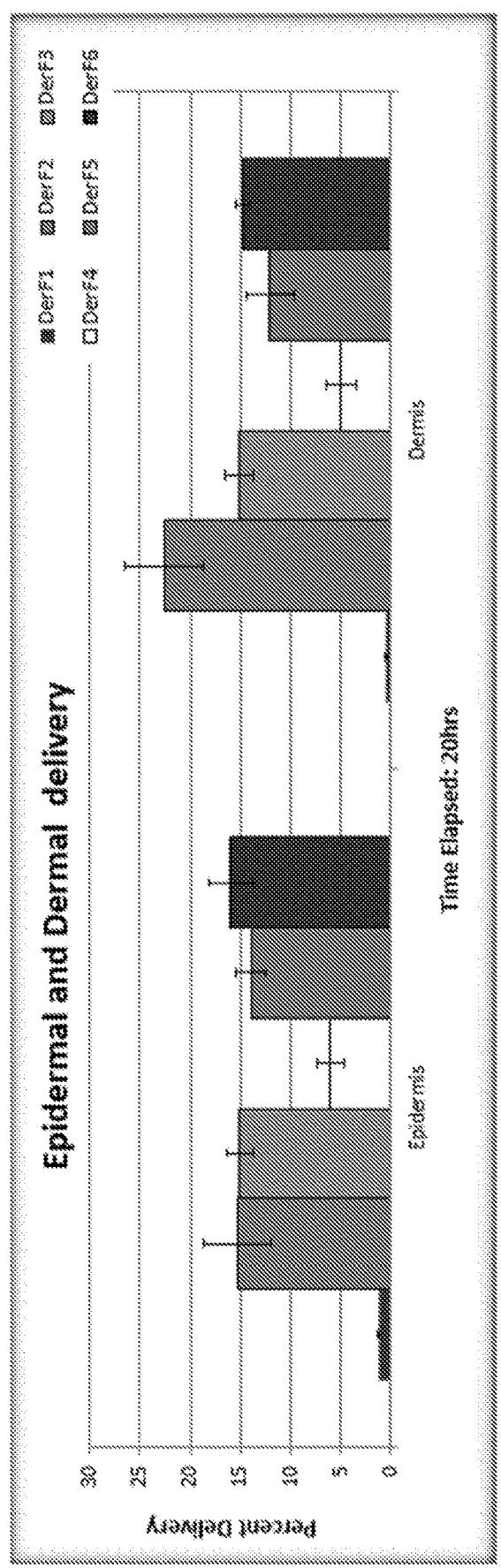
FIG. 2 is a bar chart illustrating percentage of the applied dose of succinic acid that is delivered to the epidermis and dermis at 20 hrs post application (standard error is shown; DerF6 is largest bar in Epidermis; DerF2 is largest bar in Dermis).
Figure 4:
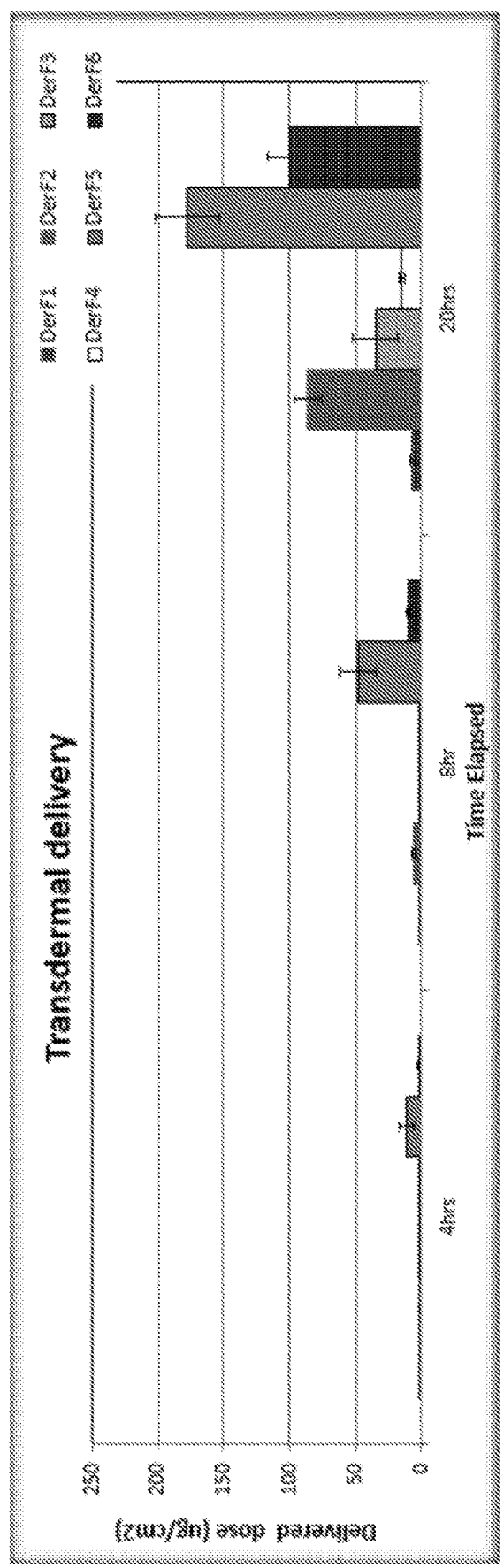
FIG. 4 is a bar chart illustrating the amount of succinic acid that is delivered transdermally in μg/cm² at 4, 8, and 20 hrs post application (standard error is shown; DerF5 is largest bar in each time point).
Figure 5:
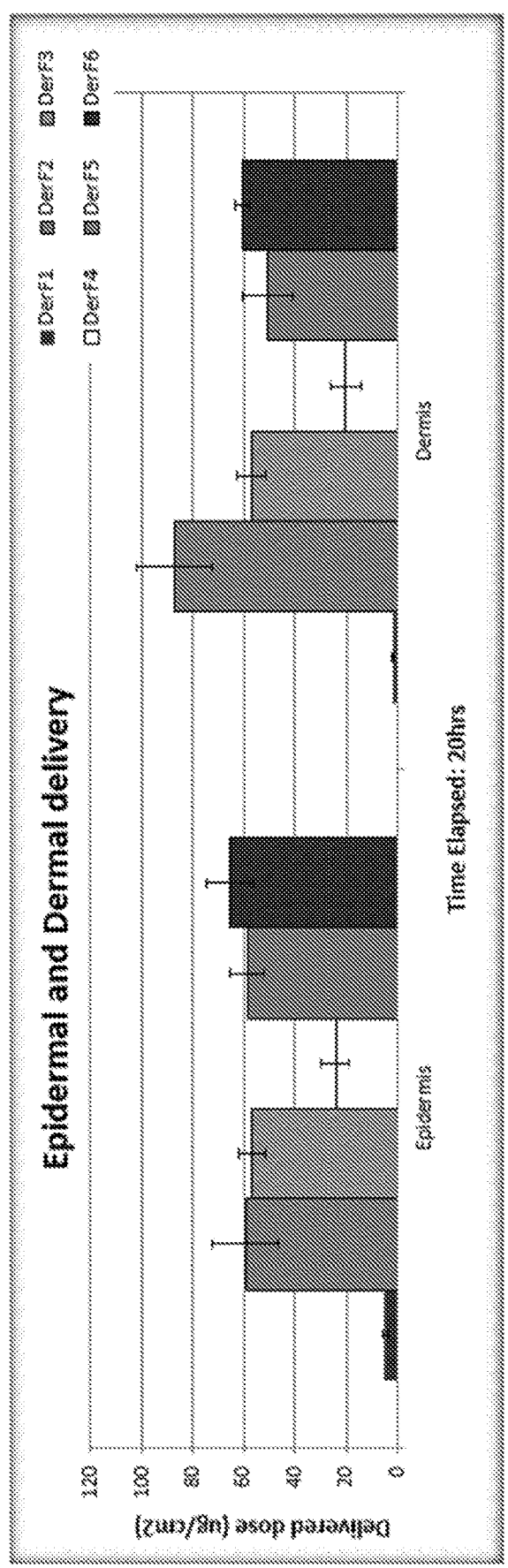
FIG. 5 is a bar chart illustrating amount of succinic acid that is delivered to the epidermis and dermis in μg/cm² at 20 hrs post application (standard error is shown; DerF6 is largest bar in Epidermis; DerF2 is largest bar in Dermis).

The results are shown in FIGS. 1-3 for delivered dose represented as percent delivery and in FIGS. 4-6 for delivered dose represented as μg/cm². As shown in the figures, formulations DerF2 and DerF3 showed the optimal delivery profile—high levels of delivery to dermis and epidermis with limited transdermal delivery across the skin.

From the data shown in FIG. 2, the improvement in delivery of succinic acid to the epidermis and dermis can be calculated as shown in Table 2 below.

TABLE 2

Calculation of Fold Increase in Percent of Succinic Acid Dose Delivered to Epidermis and Dermis in Absence and Presence of Brij ®-30.

| | DerF1 | DerF4 | DerF2 | DerF3 | DerF5 | DerF6 |
|---|---|---|---|---|---|---|
| Carrier System Present** | No | No | Yes | Yes | Yes | Yes |
| Measured Epidermis Values | 1.05* | 6.01* | 15.36* | 15.05* | 13.92* | 15.94* |
| Mean of Epidermis Values | 3.53 | | | 15.0675 | | |
| Measured Dermis Values | 0.39* | 4.99* | 22.59* | 15.08* | 12.02* | 14.85* |
| Mean of Dermis values | 2.69 | | | 16.135 | | |
| Overall Mean of Epidermis and Dermis | 3.115 | | | 15.6 | | |

TABLE 2-continued

Calculation of Fold Increase in Percent of Succinic Acid Dose
Delivered to Epidermis and Dermis in Absence and Presence of Brij ®-30.

| | DerF1 | DerF4 | DerF2 | DerF3 | DerF5 | DerF6 |
|---|---|---|---|---|---|---|
| Values Fold Difference (with vs. without Carrier System) | | | 5.0 | | | |

*Values obtained from FIG. 2.
**Carrier System included Brij ®-30 and a molecular penetration enhancer.

Thus, as shown in Table 2, delivery of succinic acid to the epidermis and dermis is substantially improved by a factor of five-fold in the presence of the Carrier System which included Brij®-30, DMSO and another molecular penetration enhancer.

Example 2

Delivery of succinic acid to epidermis and dermis in the presence of another API used for the treatment of acne using a formulation containing Brij 30 and a molecular penetration enhancer.

A topical formulation was prepared that contained 2% succinic acid, 1% salicylic acid (acne API), 15% ethanol, 15% propylene glycol, 3% Brij 30 and 15% of dimethyl isosorbide. The delivery of succinic to epidermis and dermis was tested as described in Example 1 in an independent experiment, using a different skin sample. At 22 hrs post application, 33.22% of the succinic acid dose was delivered to epidermis and dermis when Brij30 and dimethyl isosorbide were present in the formulation. In the absence of Brij30 and dimethyl isosorbide, only 7.51% was delivered which is a 4.4 fold lower amount. The preicatisence of other penetration enhancing molecules, such as Capric tryiglyceride GTCC, Polysorbate 80, Transcutol P or Polysorbate 20 did not result in enhanced delivery of succinic acid. This demonstrated that the presence of Brij30 and a molecular penetration enhancer was essential for delivery of succinic acid to the epidermis and dermis and that the presence of another API, such as salicylic acid, in the formulation did not impede delivery of succinic acid to the epidermis and dermis.

Example 3

Testing the formulation for *P. acnes* killing properties.
Formulation DerF2 described in the Table 1. was tested for antimicrobial properties against *P. acnes*, which is the main bacterium in acne involved in colonization of follicles.

*P. acnes* (ATCC 6919) was cultured on *Brucella* plates supplemented with 0.1 g/L hemin, 0.01 g/L vitamin K, and 5% (v/v) defibrinated sheep's blood at 37° C. under anaerobic conditions using a Gas-Pak (BD). For each assay, an inoculum of *P. acnes* was prepared by suspending a colony of *P. acnes* in 5 mL Reinforced *Clostridium* medium (RCM) and growing at 37° C. and 250 RPM under anaerobic conditions for 30 hours. Cultures were harvested, washed with PBS and resuspended in fresh, sterile RCM broth to a concentration of 2×106 CFU/ml.

Formulation DerF2 (50 µl) was added to wells in a 96-well plate followed by 50 µl of the prepared *P. acnes* inoculum. Plates were incubated under anaerobic conditions using a Gas-Pak (BD) for 48 hours at 37° C. Following incubation, each well was resuspended by pipetting and plated for colony counting. The plates were incubated under anaerobic conditions for 7 days. No surviving colonies were detected. This indicated that DerF2 formulation kills acne-causing bacteria that are found in hair follicles of acne subjects. The *P. acnes* killing properties in combination with penetration profiles showed that DerF2 is suitable for use as an improved acne treatment.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:
1. A topical composition for treating acne vulgaris in a subject, the composition comprising succinic acid, a non-ionic surface active agent, and a molecular penetration enhancer selected from the group consisting of DMSO, dimethyl isosorbide, lauryl lactate, isopropyl myristate and combinations thereof, in a pharmaceutically acceptable preparation, wherein
the succinic acid is present in the composition in an amount of 0.5-4 w/w %,
the nonionic surface active agent is the nonionic surface active agent is a sorbitan alkyl ester, a polyethoxylated alkyl sorbitan ester, or a polyoxypropylene glycol alkyl ether present in the composition in an amount of 3 w/w % to 5 w/w %,
the molecular penetration enhancer is present in the composition in an amount of 4-30 w/w %,
the composition is suitable for delivering to epidermis and/or dermis, an amount of succinic acid that is at least about two-fold greater than that of succinic acid in vehicle in absence of the nonionic surface active agent and the molecular penetration enhancer, and the nonionic surface active agent is a sorbitan alkyl ester, a polyethoxylated alkyl sorbitan ester, or a polyoxypropylene glycol alkyl ether.

2. The composition of claim 1, further comprising water.

3. The composition of claim 1, wherein the composition also contains another API for the treatment of acne.

4. A method of treating acne vulgaris, the method comprising topically administering to a subject in need thereof, the topical composition of claim 1.

5. The method of claim 4, wherein the amount of succinic acid delivered to epidermis and/or dermis is as least about two-fold greater than that produced by topically administering to a subject, succinic acid in vehicle in absence of the nonionic surface active agent and the molecular penetration enhancer.

6. The composition of claim 1, wherein the nonionic surface active agent is a polyoxypropylene glycol alkyl ether.

7. The method of claim 4, wherein the nonionic surface active agent is a polyoxypropylene glycol alkyl ether.

8. The method of claim 4, wherein the nonionic surface active agent is a sorbitan alkyl ester, a polyethoxylated alkyl sorbitan ester, or a polyoxypropylene glycol alkyl ether.

* * * * *